United States Patent [19]
De Vries

[11] 4,005,072
[45] Jan. 25, 1977

[54] OIL-SOLUBLE AZIRIDINYL UREA COMPOUNDS AS LUBRICATING OIL DETERGENTS

[75] Inventor: Louis De Vries, Greenbrae, Calif.

[73] Assignee: Chevron Research Company, San Francisco, Calif.

[22] Filed: Apr. 25, 1975

[21] Appl. No.: 571,885

Related U.S. Application Data

[63] Continuation of Ser. No. 5,129, Jan. 22, 1970, abandoned.

[52] U.S. Cl. .............................. 260/239 E; 208/17; 208/18; 252/32.7 R; 252/51.5 R; 260/349
[51] Int. Cl.² ...................................... C07D 203/20
[58] Field of Search ............... 260/239 E, 94.9 GB, 260/349

[56] References Cited

UNITED STATES PATENTS

| 2,265,416 | 12/1941 | Bestian | 260/239 |
| 3,247,220 | 4/1966 | Ham | 260/239 |
| 3,284,421 | 11/1966 | Breslow | 260/349 |
| 3,359,303 | 12/1967 | Coker et al. | 260/239 |
| 3,468,818 | 9/1969 | Phillips | 260/239 |
| 3,501,458 | 3/1970 | Tomalia et al. | 260/239 |
| 3,526,644 | 9/1970 | Suzuki | 260/349 |

OTHER PUBLICATIONS

Dermer et al., Ethylenimine and Other Aziridines, (Academic Press, N.Y., 1969), pp. 68–79.

Primary Examiner—Alton D. Rollins
Attorney, Agent, or Firm—G. F. Magdeburger; C. J. Tonkin; L. L. Priest

[57] ABSTRACT

Novel compositions are prepared from the thermal decomposition product of azidoformate esters reacting with aliphatic hydrocarbon olefins to form aziridine carbamates, which are then reacted with a polyamine free of primary amino groups and having at least one secondary amino group. These compositions find use as detergents and dispersants in lubricating oils and fuels, and also as emulsifiers.

4 Claims, No Drawings

OIL-SOLUBLE AZIRIDINYL UREA COMPOUNDS AS LUBRICATING OIL DETERGENTS

This is a continuation of application Ser. No. 5,129, filed Jan. 22, 1970 now abandoned.

BACKGROUND OF THE INVENTION

1. Field of the Invention

With the advent of the polyisobutenyl succinimides of alkylene polyamines, numerous and varied ashless detergents for internal combustion engines have been prepared. These compositions which comprise a long chain hydrocarbon group and a polar amine end are advantageous in lubricating oils because they do not have metals which produce ash and they are able to stably disperse deposit producing materials in the lubricating oil. Furthermore, the compositions do not in themselves lead to deposits or decompose only slowly to deposit-producing materials.

In fuels, compositions are employed which not only provide detergency in the carburetor, but aid in the removal of deposits from the intake ports and valves. In addition, preferred additives are introduced by blow-by or other mechanisms from the piston chamber into the lubricating oil in the crankcase, so as to further aid detergency and dispersancy in the lubricating oil.

2. Description of the Prior Art

Urea compositions which have found use as detergents in lubricating oils are disclosed in U.S. Pat. Nos. 3,296,128, 3,316,619 and 3,385,791.

SUMMARY OF THE INVENTION

N-carbamyl aziridines are provided wherein an aliphatic hydrocarbon group of at least 16 carbon atoms is attached to the aziridine ring. The nitrogen of the carbamyl group is bonded solely to carbon. The groups bonded to the nitrogen are free of primary amino groups and may not have secondary amino groups in the beta or gamma positions (separated by from 2 to 3 carbon atoms). These compositions find use as lubricating oil and fuel detergents and dispersants, as well as emulsifiers.

DESCRIPTION OF THE INVENTION

Detailed Compounds

Compositions are provided which are mono- or poly(carbamyl aziridines) wherein the molecular weight of the compositions varies from 352 to no greater than about 100,000. Per aziridine, there will be at least 16 carbon atoms, preferably at least 25 carbon atoms and usually not more than about 500 carbon atoms in the aliphatic hydrocarbon group or groups bonded to the carbon atoms of the aziridine ring. Usually, the compositions will have molecular weights of at least about 400 and not more than about 5,000, more usually at least about 500 and not more than about 3,500.

The number of aziridine rings will be at least 1 and usually not more than about 20, more usually not more than about 10. The preferred compositions will be monoaziridines having a total number of carbon atoms of from about 50 to 300 in the group(s) bonded to the carbon atoms of the aziridine ring. The substituents bonded on the nitrogen of the carbamyl group will have from 1 to 20 carbon atoms. Normally the total number of carbon atoms will be from 20 to 30 and there will be a total of from 0 to 8 amine nitrogen atoms. The substituents will be completely free of primary amines and also be free of secondary amines in the beta and gamma positions.

The compositions of this invention will have, for the most part, the following formula:

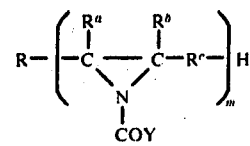

wherein
$R^1$ and $R^b$ are the same or different and are hydrogen or lower alkyl;
R is hydrogen, alkyl or alkenyl of from 16 to 500 carbon atoms, more usually of from 18 to 100 carbon atoms, but hydrogen or lower alkyl when $m$ equals 1;
$R^c$ is alkylene or alkenylene of from 16 to 500 carbon atoms, more usually of from 18 to 100 carbon atoms;
$m$ is an integer of from 1 to 20, more usually of from 1 to 10 and preferably 1;
Y is dialkyl amino, wherein the alkyl is of from 1 to 10 carbon atoms, more usually of from 1 to 6 carbon atoms; a monovalent radical of the formula:

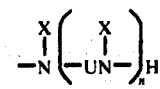

wherein
$X$ is lower alkyl (1 to 6 carbon atoms);
$n$ is an integer of from 2 to 7, more usually of from 2 to 5;
U is alkylene of from 2 to 6 carbon atoms, more usually of from 2 to 3 carbon atoms; or
a monovalent radical of the formula:

wherein
U and X are as defined previously and
$X^a$ is alkyl of from 1 to 6 carbon atoms, more usually of from 1 to 3 carbon atoms.

The preferred compositions of this invention have the following formula:

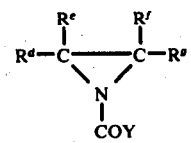

wherein
$R^{d-f}$ are the same or different and are hydrogen or lower alkyl and
$R^g$ is an aliphatic hydrocarbon group of from 16 to 300 carbon atoms, more usually of from 30 to 200 carbon atoms; preferably, $R^g$ is a branched chain aliphatic hydrocarbon group free of unsaturation, having at least 1 branch of from 1 to 2 carbon atoms per 4 carbon atoms along the chain; and Y is as defined previously.

Particularly preferred compositions are those where Y is $Y^a$ which is of the formula:

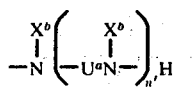

wherein $U^a$ is of from 2 to 3 carbon atoms, there being at least 2 carbon atoms between the nitrogen atoms;

$X^b$ is alkyl of from 1 to 2 carbon atoms; and $n'$ is an integer of from 2 to 4.

With aziridinyl esters prepared from monoolefins, two mols of the aziridinyl ester may be used with one mol of a polyamine having two secondary amine groups. The bis-aziridinylcarbamamides will have the following formula:

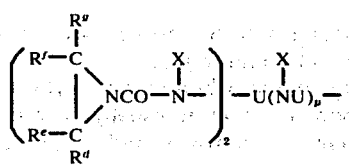

wherein $R^{a-g}$, U and X are as defined previously and $p$ is an integer of from 1 to 4.

Method of Preparation

The compositions of this invention are readily prepared by reacting a mono- or polyolefin of from 254 to 100,000 molecular weight, having at least 18 carbon atoms per olefin group, and not more than about 500 carbon atoms per olefin group, more usually having from about 18 to about 200 carbon atoms per olefin group, with an azidoformate under conditions wherein one molecule of nitrogen is lost per azido group. The alcohol radical of the ester group moiety may have any hydrocarbon group which does not interfere with the reaction. Since the group will be lost in the course of the reaction to form the product, any inexpensive convenient leaving group may be used. The hydrocarbyloxy group of the aziridine carbamate ester may be aliphatic, alicyclic, or aromatic and will normally be of from 1 to 12 carbon atoms, more usually of from 1 to 6 carbon atoms. Illustrative groups are methyl, ethyl, phenyl, benzyl, tert.-butylphenyl, cyclohexyl, tert.-butyl, etc.

The esters employed to form the products of the invention will have the following formula:

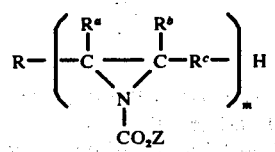

wherein

R, $R^{a-c}$ and $m$ are as defined previously and

Z is a hydrocarbon group of from 1 to 12 carbon atoms, more usually of from 1 to 7 carbon atoms, preferably of from 1 to 3 carbon atoms.

Preferred esters have the following formula:

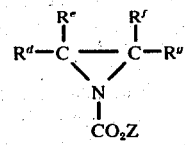

wherein $R^{d-g}$ and Z are as defined previously.

The reaction between the azidoformate ester and the olefin may be carried out thermally at temperatures in the range of 70° to 150° C., more usually 80° to 125° C. The reaction may also be carried out photochemically using ultraviolet radiation, whereby temperatures as low as −70° C. may be employed. There is no reason, however, for using such low temperatures and normally ambient temperatures will be employed for the photochemical reaction. The reaction may be carried out neat or in a suitable inert solvent, but will normally be carried out neat. The time for the reaction will vary widely depending on the reactants, the temperature, and other variables. The equivalent ratio of azidoformate to olefin will usually be at least 0.9:1 and usually not more than 2:1, more usually in the range of 1–1.5:1. The course of the reaction is easily followed by the nitrogen gas evolution. When nitrogen gas is no longer evolved, the reaction is terminated.

The olefin may be branched or straight chain, but is preferably branched and has at least 1 branch of not more than 2 carbon atoms for 4 carbon atoms along the chain, preferably at least 1 branch for 2 carbon atoms along the chain. The olefin may be internal or terminal. Preferably, the olefin will have at least 1 hydrogen, more preferred at least 2 hydrogens bonded to the olefinic carbon atoms.

Illustrative olefins which find use include octadecene, triacontene, docosene, eicosene, polyisobutylene, polypropylene, polyethylene, copolymers of isobutylene and butadiene, polybutadiene, polyisoprene, etc.

The reaction product may be worked up by conventional means, although no purification is required for the second phase.

The aziridinyl ester is then combined with a mono- or polyamine which is free of primary amino groups and does not have a second secondary amino group in the beta or gamma position to a secondary amino group. The reaction may be carried out neat or in a suitable solvent. The solvent can be conveniently chosen to have its boiling point close to the temperature of the reaction so that refluxing may be used as a temperature control. Suitable inert solvents include polyethers such as bis(2-butoxyethyl) ether, bis(2-ethoxyethyl) ether, the dimethyl ether of tris-ethyleneoxide, phenyldioxane, tertiary amines such as tributylamine, etc.

The temperature for the reaction will normally be at least 120° C. and not exceed 250° C., more usually being in the range of about 150° C. to 225° C. Depending on the other variables, the reaction time may range from 0.5 to 48 hours, more usually being from about 7 to 20 hours.

The concentration of reactants may vary from 5 to 80 weight percent of the reaction mixture and is not critical to this invention. Depending on the desired product (mono- or bis), the mols of amine to equivalents of the aziridinyl formate ester employed will generally be 0.2–5:1, more usually 0.5–3:1. For the compound having one aziridine per amine group, the ratio will normally be 1–3:1. For the bis-aziridine the ratio will be 0.2–0.5:1. For the mono-aziridine type compound with polyamines, excess amine is normally employed to avoid cross linking or bis formation.

The amines which are employed will have from 2 to 30 carbon atoms, more usually from 2 to 20 carbon atoms and from 1 to 8 amine groups, more usually from 2 to 5 amine nitrogen atoms. The polyamines will have at least 2 carbon atoms between the nitrogen atoms.

Illustrative amines include dimethylamine, diethylamine, N, N, N'-trimethylpropylenediamine, N, N', N''-trimethyldiethylenetriamine, N, N'-diethyl-2-aminoethylpiperazine, N-cyclohexylpiperazine, pyrrolidine, dipropylamine, etc.

The preferred compositions of this invention will have at least 0.01 weight percent nitrogen, more usually at least 0.5 weight percent nitrogen, and usually not more than 8.0 weight percent nitrogen, more usually not more than about 5.0 weight percent nitrogen.

The following examples are offered by way of illustration and not by way of limitation.

EXAMPLES

EXAMPLE A

To 70.0 grams (1.08 mol) sodium azide in 380 cc. water at 3° C. 100 grams (0.9 mol) ethylchloroformate in 100 cc. ether was added dropwise with fast stirring. The temperature rose to 15° C. during the addition. After stirring at 5° C. for 2½ hours, the aqueous layer was separated and extracted three times with ether. The combined ether layers were dried over magnesium sulfate and the ether removed in vacuo. Yield of the crude product, ethyl azidoformate, was 93%.

EXAMPLE I

A. Into a reaction flask was introduced 100 grams of ethyl azidoformate prepared as described in Example A and 570 grams of polyisobutylene (approximately 1,000 average molecular weight) and the mixture warmed to 40° C. With continued agitation, the temperature was slowly raised to 100° C. and the course of the reaction followed by the evolution of nitrogen gas. After 16 hours, the temperature was raised to 120° C. and maintained for an additional 8 hours. Volatile materials were than removed in vacuo. Analysis: % N, 1.4. The infrared spectrum showed strong carbonyl absorption at 1,715 cm$^{-1}$.

B. The above product was dissolved in 500 cc. of bis(2-ethoxyethyl) ether and 165 grams (2.13 equivalents) of N, N', N''-trimethyldiethylenetriamine (TMDETA) added. After heating with agitation at 120° C. for 10 hours, the temperature was raised to 175° C. and maintained for 14 hours. At the end of this time, the product was extracted three times with water. The product was then dried by azeotropic distillation with benzene. The residue was taken up in benzene and the product precipitated by the addition of methanol. Analysis: molecular weight (Thermonam), 1,387; % N, 3.58. The product showed carbonyl absorption at 1,660 cm$^{-1}$ in its infrared spectrum.

EXAMPLE II

To 570 grams of the product prepared as described in Example IA was added 116 grams (1.5 equivalents) of TMDETA and the mixture heated to 70° C. with agitation and the temperature maintained for 16 hours. The temperature was then raised to 200° C. and maintained for 8 hours. After cooling the mixture, the product was taken up in hexane and precipitated with methanol, the precipitation procedure being repeated for a total of three times. Analysis: molecular weight (Thermonam), 2,280; % N, 2.31.

EXAMPLE III

Following the procedure of Example I, into a reaction flask was introduced 700 grams of polyisobutylene (approximately 2,700 molecular weight) and 42.6 grams of ethylazidoformate and the mixture heated for 16 hours at a temperature from 100° to 110° C. followed by heating at 140° C. for 8 hours.

An aliquot of 350 grams of the above reaction mixture was taken and combined with 18 grams of TMDETA and the mixture heated at 190° C. for 16 hours followed by heating at 200° C. for 6 hours. The product was then taken up in pentane and precipitated with methanol and the procedure repeated for a total of 3 times. Analysis: % N, 1.2.

As already indicated, the compositions of this invention find use as detergents and dispersants in lubricating oils and are found to be effective under a wide variety of conditions; not only under the hot conditions of the diesel engine, but the much more variable temperature conditions of the automobile engine.

The compositions of this invention may be formulated with various lubricating fluids (hereinafter referred to as oils) which are derived either from natural or synthetic sources. Oils generally have viscosities of from about 35 to 50,000 Saybolt Universal Seconds (SUS) at 100° F.

Among natural hydrocarbonaceous oils are paraffin base, naphthenic base, asphaltic base and mixed base oils.

Illustrative of synthetic oils are hydrocarbon oils, such as polymers of various olefins, generally from 2 to 8 carbon atoms and alkylated aromatic hydrocarbons, and nonhydrocarbon oils, such as polyalkylene oxides, aromatic ethers, carboxyl esters, phosphate esters, and silicon esters. The preferred media are the hydrocarbonaceous media, both natural and synthetic.

The above oils may be used individually or together whenever miscible or made so by the use of mutual solvents.

When the detergents of this invention are compounded with lubricating oils for use in an engine, the detergents will be present in at least about 0.1 weight percent and usually not more than 20 weight percent, more usually in the range of about 1 to 15 weight percent. The compounds can be prepared as concentrates due to their excellent compatibility with oils. As concentrates, the compounds of this invention will generally range from about 10 to 70 weight percent, more usually from about 20 to 50 weight percent of the total composition.

A preferred aspect in using the compounds of this invention in lubricating oils is to include in the oil from about 1 to 50 mM./kg of a dihydrocarbyl phosphorodithioate, wherein the hydrocarbyl groups are from about 4 to 36 carbon atoms. Usually, the hydrocarbyl groups will be alkyl or alkaryl groups. The remaining valence of the phosphorodithioate will usually be satisfied by zinc, but polyalkyleneoxy or a third hydrocarbyl group may also be used. (Hydrocarbyl is an organic radical composed solely of carbon and hydrogen which may be aliphatic, alicyclic, or aromatic or combinations thereof.)

Other additives may also be included in the oil such as pour point depressants, oiliness agents, antioxidants, rust inhibitors, etc. Usually, the total amount of these additives will range from about 0.1 to 10 weight percent, more usually from about 0.5 to 5 weight percent. The individual additives may vary from about 0.01 to 5 weight percent of the composition.

In order to demonstrate the excellent effectiveness of the compounds of this invention as detergents and dispersants, the exemplary composition of Example III was tested in two different engine tests. The results for a commercially available ashless detergent are also reported.

In the Sequence Vb test (see Table I infra for description), the exemplary composition was employed at 8.2 weight percent. Included in the compounded lubricating oil composition was 50 mM./kg (based on calcium) of an overbased calcium sulfonate having a 9.3 base ratio and 11.4 weight percent calcium and 15 mM./kg of dialkyldithiophosphate (alkyl of from 4 to 5 carbon atoms) in a mid-continent 130 neutral oil. For comparative purposes, the commercial ashless detergent was used at 7.2 weight percent, the difference in the amount of additive not significantly affecting the difference in result.

The following table indicates the results obtained.

TABLE I

| | Sequence Vb Results[1] | | |
|---|---|---|---|
| | Piston[2] Varnish | Total[3] Varnish | Total[3] Sludge |
| Example III | 8.4 | 38.4 | 45.7 |
| Commercial Detergent | 7.9 | 37.9 | 44.0 |

[1]Description of the test is found in A. Schilling, Motor Oil and Engine Lubrication, Scientific Publications (GB) LTD (1968), 2nd ed., pp 3.35.
[2]Rating 0–10, 10 being clean
[3]Rating 0–50, 50 being clean An additional test was carried out which is the Ford Varnish test. The same formulation was used as described for the Sequence Vb test. The conditions for the test are as follows:

The engine employed is a 1967 Ford 240 CID engine with a single barrel carburetor. The engine is fitted with an oil pan water spray for oil temperature control and an emission control system which aspirates the crankcase fuels and is controlled to 2 inches of water negative pressure. Maximum bore out-of-roundness is 0.001 inch, maximum bore taper is 0.002 inch and only pistons which have a skirt cam drop of 0.0050 inch ± 0.0008 inch are employed. The test fuel is a regular commercial gasoline combined with FCC heavy gasoline leaded to 2.5 ml/gallon of TEL which gives a piston varnish number of 6.4 (± 0.4 SD numbers) when run in a test engine using a standard compounded reference oil. The engine is flushed by adding two quarts of test oil and operating at 1,500 rpm and 15 inches of manifold vacuum for 5 minutes. The engine is then drained and refilled with 8 pounds of test oil and the run carried out for 60 hours. At 20 and 40 hours, the engine is shut down, the oil is drained and an 8 dram sample taken. Seven pounds of used oil and 1 pound of fresh oil is then added to the engine. The conditions of the test follow the following cycle:

| Specifications | Stage I | Stage II | Stage III |
|---|---|---|---|
| Time, Min. | 45 | 120 | 75 |
| Speed, rpm | 500 ± 25 | 2500 ± 25 | 2500 ± 25 |
| Load, bhp[1] | None | 71.9 ± 1.0 | 71.9 ± 1.0 |
| Oil Temperature, °F. | 120 ± 2 | 175 ± 2 | 201 ± 2 |
| Water Out Temperature, °F. | 115 ± 2 | 125 ± 2 | 171 ± 2 |
| Air/Fuel Ratio, Lb Air/Lb Fuel | 9.5 ± 0.1 | 15.5 ± 0.1 | 15.5 ± 0.1 |
| Spark Advance, Degrees | 6 | 20 | 20 |
| Blow-by | Record | Record | Record |
| Intake Air Temperature, °F. | 100 ± 2 | 100 ± 2 | 100 ± 2 |

[1]Proportioned from 289 cubic inches = 86.6 ± 1.0 to 240 cubic inches = 71.9 ± 1.0

For the exemplary composition of Example III, the results for piston varnish based on a rating of 0–10, 10 being clean, were 8.7 and 8.4. For the commercial succinimide, the result was 6.9.

It is evident from the above results that the subject compositions of this invention provide excellent detergency and dispersancy as well as protection from varnish. Furthermore, these compositions can be used in fuels to provide detergent action.

When the additives of this invention are used in fuels, the fuel normally will be a hydrocarbon base liquid. The additive may be prepared as a concentrate, using a suitable hydrocarbon or alcohol solvent boiling in the range of about 150° to 400° F. Preferably, an aromatic hydrocarbon solvent is used, such as benzene, toluene, xylene or higher boiling aromatics of aromatic thinners. Aliphatic alcohols of about 3 to 8 carbon atoms, such as isopropanol, isobutylcarbinol, n-butanol and the like, in combination with hydrocarbon solvents are also suitable for use with the detergent additive. In the concentrate, the amount of the additive will be ordinarily at least 10 percent by weight and generally not exceed 70 percent by weight.

The amount of the detergent used in the fuel will generally be from about 30 to 1,000 ppm.

In gasoline fuels, other fuel additives may also be included such as antiknock agents, e.g., tetramethyl lead or tetraethyl lead. Also included may be lead scavengers such as aryl halides, e.g., dichlorobenzene or alkyl halides, e.g., ethylene dibromide.

A nonvolatile lubricating mineral oil, e.g., petroleum spray oil, particularly a refined naphthenic lubricating oil having a viscosity at 100° F. of 1,000 to 2,000 SUS, is a suitable additive for the gasoline compositions used with the detergents of this invention and its use is preferred. These oils are believed to act as a carrier for the detergent and assist in removing and preventing deposits. They are employed in amounts from about 0.05 to 0.5 percent by volume, based on the final gasoline composition.

The compositions of this invention provide ashless detergency to lubricating oils and fuels, helping to keep motors operating free of deposits, thus avoiding the concommitant problems that come from sticking rings and valves. Deposits are maintained stably dispersed in lubricating oils to provide smooth performance of internal combustion engines. Internal combustion engines can be employed for longer periods of time without tune-up, providing optimum performance in utilization of fuel and production of power.

I claim:

1. A compound of the formula

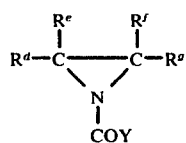

wherein $R^{d-f}$ are the same or different and are hydrogen or lower alkyl;

$R^g$ is a branched chain aliphatic hydrocarbon group free of unsaturation containing 30–200 carbon atoms and having at least 1 branch of from 1 to 2 carbon atoms per 4 carbon atoms along the chain; and Y is a monovalent radical of the formula

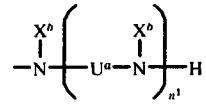

wherein $U^a$ is an alkylene of from 2–3 carbon atoms, there being at least 2 carbon atoms between nitrogen atoms, $X^b$ is an alkyl of from 1–2 carbon atoms, and $n^1$ is an integer of from 2–4.

2. A compound of claim 1 wherein $R^g$ is polyisobutylene, and $U^a$ contains 2 carbon atoms.

3. A compound of claim 2 wherein $X^b$ is methyl and $n^1$ is 2.

4. A compound of claim 3 wherein $R^g$ is polyisobutylene of from about 1000 to about 2700 average molecular weight.

* * * * *